(12) United States Patent
Yao et al.

(10) Patent No.: US 11,779,264 B2
(45) Date of Patent: Oct. 10, 2023

(54) DARK CIRCLE DETECTION AND EVALUATION METHOD AND APPARATUS

(71) Applicant: Honor Device Co., Ltd., Guangdong (CN)

(72) Inventors: Ye Yao, Shenzhen (CN); Chen Dong, Shenzhen (CN); Xin Ding, Shenzhen (CN); Hongwei Hu, Shenzhen (CN); Wenmei Gao, Shenzhen (CN)

(73) Assignee: Honor Device Co., Ltd., Shenzhen (CN)

( * ) Notice: Subject to any disclaimer, the term of this patent is extended or adjusted under 35 U.S.C. 154(b) by 263 days.

(21) Appl. No.: 17/297,684

(22) PCT Filed: Nov. 15, 2019

(86) PCT No.: PCT/CN2019/118635
§ 371 (c)(1),
(2) Date: May 27, 2021

(87) PCT Pub. No.: WO2020/108322
PCT Pub. Date: Jun. 4, 2020

(65) Prior Publication Data
US 2022/0019765 A1 Jan. 20, 2022

(30) Foreign Application Priority Data

Nov. 29, 2018 (CN) .......................... 201811446411.8

(51) Int. Cl.
*A61B 5/103* (2006.01)
*A61B 5/00* (2006.01)
(Continued)

(52) U.S. Cl.
CPC ............ *A61B 5/441* (2013.01); *A61B 5/1032* (2013.01); *A61B 5/444* (2013.01); *G06V 10/25* (2022.01);
(Continued)

(58) Field of Classification Search
CPC ....... A61B 5/441; A61B 5/1032; A61B 5/444; G06V 10/25; G06V 30/18105; G06V 40/171; G06V 40/193; G06V 40/172
(Continued)

(56) References Cited

U.S. PATENT DOCUMENTS

2015/0313532 A1* 11/2015 Marinkovich ......... A61B 5/486
600/306
2016/0125228 A1 5/2016 Son et al.
(Continued)

FOREIGN PATENT DOCUMENTS

CN 105844242 A 8/2016
CN 107392841 A 11/2017
(Continued)

OTHER PUBLICATIONS

Roshaslinie Ramli et al., "Segmentation of Acne Vulgaris Lesions," 2011 International Conference on Digital Image Computing: Techniques and Applications, pp. 335-339, total 5 pages (Dec. 31, 2011).
(Continued)

*Primary Examiner* — Ali Bayat
(74) *Attorney, Agent, or Firm* — Leydig, Voit & Mayer, Ltd.

(57) ABSTRACT

A dark circle detection and evaluation method includes: obtaining a to-be-processed image; extracting a dark circle region of interest from the to-be-processed image; performing color clustering on the dark circle region of interest to obtain n types of colors in the dark circle region of interest, where n is a positive integer; recognizing a dark circle region in the dark circle region of interest based on the n types of colors; and obtaining a dark circle evaluation result based on the dark circle region.

20 Claims, 5 Drawing Sheets

(51) Int. Cl.
*G06V 40/16* (2022.01)
*G06V 40/18* (2022.01)
*G06V 10/25* (2022.01)
*G06V 30/18* (2022.01)

(52) U.S. Cl.
CPC ...... *G06V 30/18105* (2022.01); *G06V 40/171* (2022.01); *G06V 40/193* (2022.01)

(58) Field of Classification Search
USPC .......................................................... 382/103
See application file for complete search history.

(56) References Cited

U.S. PATENT DOCUMENTS

2016/0125229 A1    5/2016  Soare
2017/0079599 A1*   3/2017  Yoshida ................ G06T 7/0012
2017/0184442 A1*   6/2017  Satish ..................... A61M 1/76
2017/0246473 A1*   8/2017  Marinkovich .......... G16H 30/40
2018/0047186 A1*   2/2018  Sato ........................ G06T 11/60

FOREIGN PATENT DOCUMENTS

CN    107730456 A    2/2018
CN    108830184 A    11/2018
TW    201106919 A1   3/2011

OTHER PUBLICATIONS

Manish Kumar et al., "An Intelligent System to Diagnosis the Skin Disease," ARPN Journal of Engineering and Applied Sciences, vol. 11, No. 19, pp. 11368-11373, total 6 pages (Oct. 31, 2016).

* cited by examiner

DARK CIRCLE DETECTION AND EVALUATION METHOD AND APPARATUS

CROSS-REFERENCE TO RELATED APPLICATIONS

This patent application is a U.S. national phase of International Application No. PCT/CN2019/118635, filed Nov. 15, 2019, which claims the benefit of Chinese Patent Application No. 201811446411.8, filed on Nov. 29, 2018, both of which are hereby incorporated by reference in their entireties.

TECHNICAL FIELD

Embodiments of this application relate to the image processing field, and more specifically, to a method and a dark circle detection and evaluation apparatus.

BACKGROUND

With promotion of science and technology and improvement of people's quality of life, facial skin quality as a mirror of physical health of the human body, has attracted increasing attention.

Generally speaking, the facial skin quality can be evaluated in eight dimensions: fine lines, pores, blackheads, a blush region, freckle, skin age, nasolabial folds, and dark circles. Dark circles rank high among users' concerns about facial skin. Especially for female users, dark circles have always been a facial skin problem of great concern.

Therefore, how to effectively detect and evaluate dark circles has become an urgent problem to be solved.

SUMMARY

This application provides a method and a dark circle detection and evaluation apparatus, to effectively detect and evaluate a dark circle region in an image.

According to a first aspect, a dark circle detection and evaluation method is provided, where the method includes: obtaining a to-be-processed image; extracting a dark circle region of interest from the to-be-processed image; performing color clustering on the dark circle region of interest to obtain n types of colors in the dark circle region of interest, where n is a positive integer; recognizing a dark circle region in the dark circle region of interest based on the n types of colors; and obtaining a dark circle evaluation result based on the dark circle region.

According to the method in this embodiment of this application, the dark circle region of interest is extracted from the to-be-processed image, color clustering is performed on the dark circle region of interest to obtain the n types of colors, the dark circle region in the dark circle region of interest is precisely recognized based on the n types of colors, and the dark circle evaluation result is obtained based on the dark circle region. In this way, the dark circle region in the image can be effectively detected and evaluated.

In a possible implementation, the recognizing a dark circle region in the dark circle region of interest based on the n types of colors includes: determining a dark circle color and a reference skin color based on the n types of colors; and determining the dark circle region in the dark circle region of interest based on the dark circle color and the reference skin color.

In a possible implementation, a first color in the n types of colors is determined as the dark circle color in the dark circle region of interest; and a second color in the n types of colors is determined as the reference skin color in the dark circle region of interest.

In a possible implementation, the first color is a darkest color obtained after noise is removed from the n types of colors, and the second color is a lightest color obtained after bright light is removed from the n types of colors.

In a possible implementation, the determining the dark circle region in the dark circle region of interest based on the dark circle color and the reference skin color includes: If a first pixel in the dark circle region of interest satisfies:

$$\frac{C - CD}{CS - C} < T1,$$

where the first pixel belongs to the dark circle region, where C is the first pixel, CD is the dark circle color, CS is the reference skin color, and T1 is a contrast of the first pixel with respect to the dark circle color and the reference skin color.

In a possible implementation, a first pixel in the dark circle region of interest satisfies:

$$CS - C >= T2,$$

where C is the first pixel, CS is the reference skin color, and T2 represents a minimum contrast between two colors between which human eyes can distinguish.

In a possible implementation, the reference skin color satisfies at least one of:

$$CS < T3 \text{ or } CS - CS_{i-1} <= T4,$$

where CS is the reference skin color; CS belongs to an $i^{th}$ type of color in the n types of colors, and $CS_{i-1}$ is an $(i-1)^{th}$ type of color in the n types of colors, where i is a positive integer greater than or equal to 1 and less than or equal to n; T3 represents a minimum value of a color of a bright light region; and T4 represents a difference between the $i^{th}$ type of color and the $(i-1)^{th}$ type of color.

In a possible implementation, the extracting a dark circle region of interest from the to-be-processed image includes: removing an eyelash region from the to-be-processed image; and extracting the dark circle region of interest from the to-be-processed image from which the eyelash region is removed.

In a possible implementation, the obtaining a dark circle evaluation result based on the dark circle region includes: extracting a feature of the dark circle region, where the feature includes at least one of a contrast of the dark circle region, an area of the dark circle region, or a variance of the dark circle region; and evaluating, based on the feature, a severity of dark circles by using a pattern recognition method.

In a possible implementation, the obtaining a dark circle evaluation result based on the dark circle region includes: determining a type of dark circles based on a location of a region of a darkest color in the n types of colors and/or a color of the dark circle region.

In a possible implementation, the dark circle region includes j regions, the j regions one-to-one correspond to j types of colors in the n types of colors, and j is an integer greater than or equal to 1 and less than n. The method further includes: extracting a Y value, a CR value, and a CB value of each type of color in the j types of colors, where the Y value represents brightness of each type of color, the CR value represents a difference between a red component of each type of color and the brightness of each type of color, and the CB value represents a difference between a blue component of each type of color and the brightness of each type of color; and determining, based on the Y value, the CR value, and the CB value of each type of color, that a type of dark circles included in a region corresponding to each type of color is pigmented dark circles or vascular dark circles, where the vascular dark circles include red eye circles, dark-cyan dark circles, light-cyan dark circles, light-red dark circles, or blue eye circles.

In a possible implementation, the method further includes: If a color of a middle region in the dark circle region of interest is darker than the dark circle color, the color of the middle region is darker than a color of a region surrounding the middle region, and the middle region is a non-discrete region, the dark circle region includes structural dark circles.

In a possible implementation, the method further includes: If the dark circle region includes at least two types of dark circles in the vascular dark circles, the pigmented dark circles, or the structural dark circles, dark circles in the dark circle region are mixed dark circles.

According to a second aspect, a dark circle detection and evaluation apparatus is provided, where the apparatus includes: an obtaining module, configured to obtain a to-be-processed image; and a processing module, configured to extract a dark circle region of interest from the to-be-processed image, where the processing module is configured to perform color clustering on the dark circle region of interest to obtain n types of colors in the dark circle region of interest, and n is a positive integer; the processing module is configured to recognize a dark circle region in the dark circle region of interest based on the n types of colors; and the processing module is configured to obtain a dark circle evaluation result based on the dark circle region.

According to the apparatus in this embodiment of this application, the dark circle region of interest is extracted from the to-be-processed image, color clustering is performed on the dark circle region of interest to obtain the n types of colors, the dark circle region in the dark circle region of interest is precisely recognized based on the n types of colors, and the dark circle evaluation result is obtained based on the dark circle region. In this way, the dark circle region in the image can be effectively detected and evaluated.

In a possible implementation, the processing module is specifically configured to: determine a dark circle color and a reference skin color based on the n types of colors; and determine the dark circle region in the dark circle region of interest based on the dark circle color and the reference skin color.

In a possible implementation, the processing module is specifically configured to: determine a first color in the n types of colors as the dark circle color in the dark circle region of interest; and determine a second color in the n types of colors as the reference skin color in the dark circle region of interest.

In a possible implementation, the first color is a darkest color obtained after noise is removed from the n types of colors, and the second color is a lightest color obtained after bright light is removed from the n types of colors.

In a possible implementation, the processing module is specifically configured to: If a first pixel in the dark circle region of interest satisfies:

$$\frac{C-CD}{CS-C} < T1,$$

where the first pixel belongs to the dark circle region, where C is the first pixel, CD is the dark circle color, CS is the reference skin color, and T1 is a contrast of the first pixel with respect to the dark circle color and the reference skin color.

In a possible implementation, a first pixel in the dark circle region of interest satisfies:

$$CS-C >= T2,$$

where C is the first pixel, CS is the reference skin color, and T2 represents a minimum contrast between two colors between which human eyes can distinguish.

In a possible implementation, the reference skin color satisfies at least one of:

$$CS < T3 \text{ or } CS - CS_{i-1} <= T4,$$

where CS is the reference skin color; CS belongs to an $i^{th}$ type of color in the n types of colors, and $CS_{i-1}$ is an $(i-1)^{th}$ type of color in the n types of colors, where i is a positive integer greater than or equal to 1 and less than or equal to n; T3 represents a minimum value of a color of a bright light region; and T4 represents a difference between the type of color and the $(i-1)^{th}$ type of color.

In a possible implementation, the processing module is specifically configured to: remove an eyelash region from the to-be-processed image; and extract the dark circle region of interest from the to-be-processed image from which the eyelash region is removed.

In a possible implementation, the processing module is specifically configured to: extract a feature of the dark circle region, where the feature includes at least one of a contrast of the dark circle region, an area of the dark circle region, or a variance of the dark circle region; and evaluate, based on the feature, a severity of dark circles by using a pattern recognition method.

In a possible implementation, the processing module is specifically configured to determine a type of dark circles based on a location of a region of a darkest color in the n types of colors and/or a color of the dark circle region.

In a possible implementation, the dark circle region includes j regions, the j regions one-to-one correspond to j types of colors in the n types of colors, and j is an integer greater than or equal to 1 and less than n. The processing module is further configured to: extract a Y value, a CR value, and a CB value of each type of color in the j types of colors, where the Y value represents brightness of each type of color, the CR value represents a difference between a red component of each type of color and the brightness of each type of color, and the CB value represents a difference between a blue component of each type of color and the brightness of each type of color; and determine, based on the Y value, the CR value, and the CB value of each type of color, that a type of dark circles included in a region corresponding to each type of color is pigmented dark circles or vascular dark circles, where the vascular dark circles include red eye circles, dark-cyan dark circles, light-cyan dark circles, light-red dark circles, or blue eye circles.

In a possible implementation, if a color of a middle region in the dark circle region of interest is darker than the dark circle color, the color of the middle region is darker than a color of a region surrounding the middle region, and the middle region is a non-discrete region, the dark circle region includes structural dark circles.

In a possible implementation, if the dark circle region includes at least two types of dark circles in the vascular dark circles, the pigmented dark circles, or the structural dark circles, dark circles in the dark circle region are mixed dark circles.

The modules included in the apparatus in the second aspect may be implemented by using software and/or hardware.

For example, the modules included in the apparatus in the second aspect may be implemented by using a processor. To be specific, the apparatus in the second aspect may include a processor, and the processor is configured to execute a program instruction, to implement functions that can be implemented by the modules included in the apparatus.

Optionally, the apparatus in the second aspect may further include a memory, configured to store the program instruction executed by the processor, and even configured to store various types of data.

Optionally, the apparatus in the second aspect may be a chip that can be integrated into a smart device. In this case, the apparatus may further include a communications interface.

According to a third aspect, this application provides a computer-readable storage medium. The computer-readable storage medium stores program code executed by a dark circle detection and evaluation apparatus. The program code includes an instruction used to perform the method in any one of the first aspect or the possible implementations of the first aspect.

According to a fourth aspect, this application provides a computer program product including an instruction. When the computer program product runs on a dark circle detection and evaluation apparatus, the apparatus is enabled to perform the method in any one of the first aspect or the possible implementations of the first aspect.

According to the method in this embodiment of this application, the dark circle region of interest is extracted from the to-be-processed image, color clustering is performed on the dark circle region of interest to obtain the n types of colors, the dark circle region in the dark circle region of interest is precisely recognized based on the n types of colors, and the dark circle evaluation result is obtained based on the dark circle region. In this way, the dark circle region in the image can be effectively detected and evaluated.

DESCRIPTION OF EMBODIMENTS

The following describes technical solutions of this application with reference to accompanying drawings.

The technical solutions in the embodiments of this application may be applied to various terminal devices that can perform image processing. The terminal device may be specifically a camera, a smartphone, or another terminal device or apparatus that can perform image processing. This is not limited in the embodiments of this application.

In the embodiments of this application, a terminal device or a network device includes a hardware layer, an operating system layer running above the hardware layer, and an application layer running above the operating system layer. The hardware layer includes hardware such as a central processing unit (CPU), a memory management unit (MMU), and a memory (also referred to as a main memory). The operating system may be any one or more computer operating systems that implement service processing by using a process, for example, a Linux operating system, a Unix operating system, an Android operating system, an iOS operating system, or a Windows operating system. The application layer includes applications such as a browser, an address book, word processing software, and instant messaging software. In addition, a specific structure of an execution body of a method provided in the embodiments of this application is not particularly limited in the embodiments of this application, provided that a program that records code of the method provided in the embodiments of this application can be run to perform communication according to the method provided in the embodiments of this application. For example, the execution body of the method provided in the embodiments of this application may be a terminal device or a network device, or a functional module that is in a terminal device or a network device and that can invoke and execute the program.

In addition, aspects or features of this application may be implemented as a method, an apparatus or a product that uses standard programming and/or engineering technologies. The term "product" used in this application covers a computer program that can be accessed from any computer-readable component, carrier, or medium. For example, the computer-readable medium may include but is not limited to: a magnetic storage component (for example, a hard disk, a floppy disk, or a magnetic tape), an optical disc (for example, a compact disc (CD) or a digital versatile disc (DVD)), a smart card, and a flash memory component (for example, an erasable programmable read-only memory (EPROM), a card, a stick, or a key drive). In addition, various storage media described in this specification may represent one or more devices and/or other machine-readable media that are configured to store information. The term "machine-readable media" may include but is not limited to a radio channel, and various other media that can store, contain, and/or carry an instruction and/or data.

Figure 1:
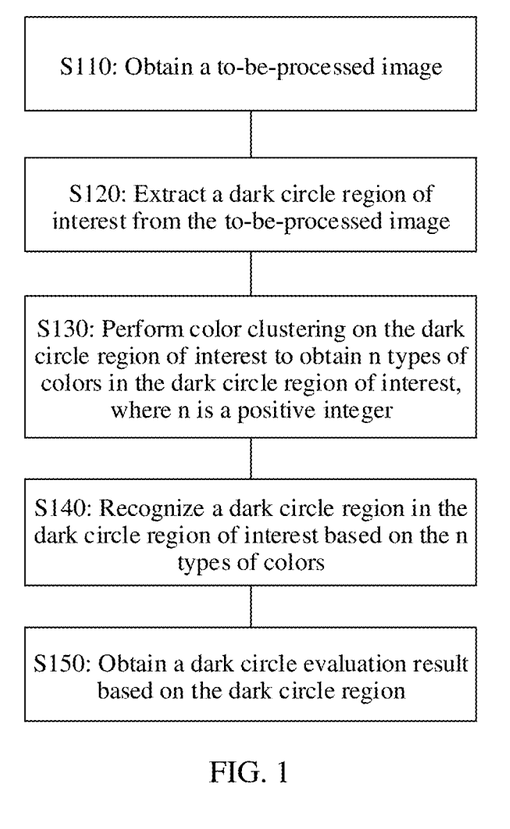
FIG. 1 is a schematic flowchart of a dark circle detection and evaluation method according to an embodiment of this application.

FIG. 1 is a schematic flowchart of a method 100 for detecting and evaluating dark circles according to an embodiment of this application. It should be understood that FIG. 1 shows steps or operations of the communication method, but these steps or operations are merely examples. In this embodiment of this application, other operations or variations of the operations in FIG. 1 may be alternatively performed, not all the steps need to be performed, or the steps may be performed in another sequence.

S110: Obtain a to-be-processed image.

Figure 2:
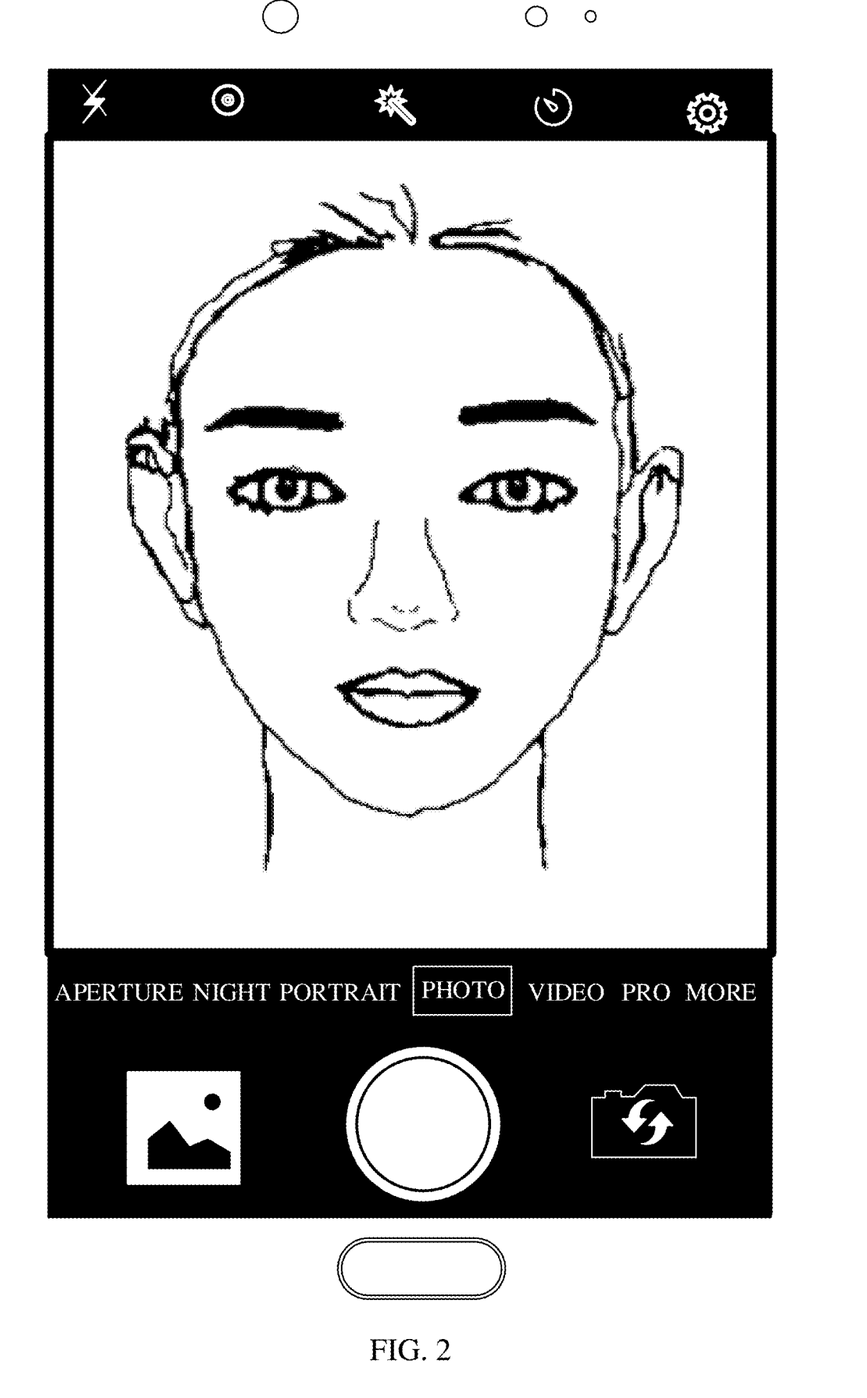
FIG. 2 is a schematic block diagram of a display interface according to an embodiment of this application.

The to-be-processed image should include an eye region of a user. For example, as shown in FIG. 2, the to-be-processed image may be a face image of the user.

In this embodiment of this application, a terminal device configured to perform the method 100 for detecting and evaluating dark circles may be a terminal device with a photographing function, such as a camera or a smartphone.

Optionally, the user may perform shooting by using the terminal device, to obtain the to-be-processed image.

S120: Extract a dark circle region of interest from the to-be-processed image.

In this embodiment of this application, the terminal device may recognize a facial feature point in the to-be-processed image by using a facial recognition technology, and extract the dark circle region of interest (ROI) from the to-be-processed image based on a location of the facial feature point. For a specific facial recognition method, refer to the conventional technology. Details are not described in this embodiment of this application.

Optionally, the dark circle region of interest may be extracted based on a key eye feature point included in the facial feature point. The dark circle region of interest may include all dark circle regions of lower eyelids and a reference skin color region.

In this embodiment of this application, an eyelash region may be removed from the to-be-processed image.

Optionally, different skin colors may correspond to different thresholds. A threshold corresponding to a skin color in the dark circle region of interest is determined, and then eyelashes are removed based on the threshold.

Optionally, the dark circle region of interest may be extracted from the to-be-processed image from which the eyelash region is removed.

In this embodiment of this application, filtering may be performed on the to-be-processed image to remove noise from the to-be-processed image. For a specific filtering method, refer to the conventional technology. Details are not described in this embodiment of this application.

S130: Perform color clustering on the dark circle region of interest to obtain n types of colors in the dark circle region of interest, where n is a positive integer.

Figure 3:
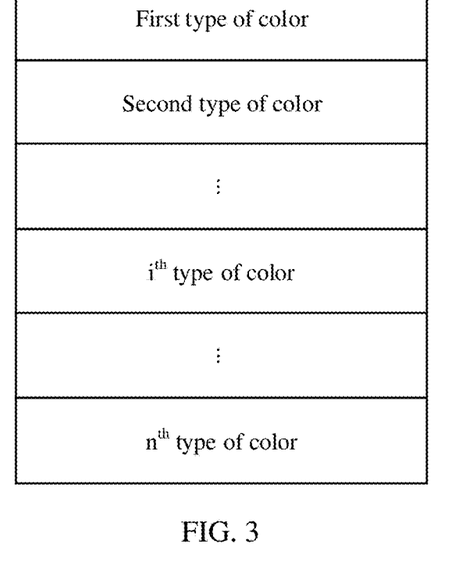
FIG. 3 is a schematic block diagram of clustering processing according to an embodiment of this application.

In this embodiment of this application, the n types of colors obtained after clustering may be those shown in FIG. 3, that is, they are sequentially a first type of color to an $n^{th}$ type of color from top to bottom. Optionally, the n types of colors obtained after clustering may alternatively be the first type of color to the $n^{th}$ type of color sequentially from bottom to top.

Optionally, the n types of colors may be distributed from the first type of color to the $n^{th}$ type of color in descending order by darkness. Colors of pixels included in an $i^{th}$ type of color in the n types of colors are the same or similar. That is, differences between grayscale values of different pixels in the $i^{th}$ type of color meet a specific threshold range, where i is a positive integer greater than or equal to 1 and less than or equal to n.

In this embodiment of this application, color clustering may be performed on the dark circle region of interest by using a k-means clustering algorithm, a fuzzy c-means clustering algorithm, or the like. This is not limited in this embodiment of this application.

S140: Recognize a dark circle region in the dark circle region of interest based on the n types of colors.

In this embodiment of this application, a dark circle color and a reference skin color may be determined based on the n types of colors.

In this embodiment of this application, a first color in the n types of colors may be determined as the dark circle color in the dark circle region of interest. It should be understood that the first color may be a darkest color in the dark circle region of interest after noise is removed from the dark circle region of interest, and the noise may be a region that is darker than dark circles, such as a freckle, a mole, or an eyelash.

Optionally, the first color may be a darkest color in the n types of colors.

For example, after color clustering is performed on the dark circle region of interest, a region of the darkest color in an upper left corner of the to-be-processed image may be used as a starting position of dark circles. The part of the darkest color needs to have a specific quantity of pixels to prevent an impact of a small amount of noise.

In this embodiment of this application, a second color in the n types of colors may be determined as the reference skin color in the dark circle region of interest. It should be understood that the second color may be a lightest color in the dark circle region of interest after bright light is removed from the dark circle region of interest. Usually, the bright light may refer to a region lighter than the reference skin color.

Optionally, the second color may be a lightest color in the n types of colors.

In a possible implementation, to avoid that pixels in a bright light or low light region are determined as the reference skin color, the reference skin color needs to satisfy at least one of:

$$CS < T3 \text{ or } CS - CS_{i-1} <= T4,$$

where CS is the reference skin color; CS belongs to the $i^{th}$ type of color in the n types of colors, $CS_{i-1}$ is an $(i-1)^{th}$ type of color in the n types of colors, and i is a positive integer greater than or equal to 1 and less than or equal to n; T3 represents a minimum value of a color of the bright light region; and T4 represents a difference between the $i^{th}$ type of color and the $(i-1)^{th}$ type of color. Optionally, T4 may be a maximum difference between the $i^{th}$ type of color and the $(i-1)^{th}$ type of color.

In this embodiment of this application, bright light may be removed by using the following method.

A lightest color in the dark circle region of interest is obtained, and it is determined whether the lightest color is the bright light. If the lightest color is greater than or equal to T3, and a difference between the lightest color and an adjacent cluster color is greater than T4, it indicates that the current lightest color is the bright light. In this case, the bright light (that is, the current lightest color) is removed. Then, a current lightest color in the dark circle region of interest existing after the bright light is removed is obtained, and then it is determined whether the current lightest color is the bright light (iteration goes on until a current lightest color is not the bright light). If the lightest color is not greater than or equal to T3, or a difference between the lightest color and an adjacent cluster color is not greater than T4, it indicates that the current lightest color is the reference skin color (that is, the current lightest color is not the bright light, and in this case, the iteration ends). In this case, bright light removal ends.

That is, the reference skin color needs to satisfy at least one of:

$$CS < T3$$

or $$CS - CS_{i-1} <= T4.$$

Figure 4:
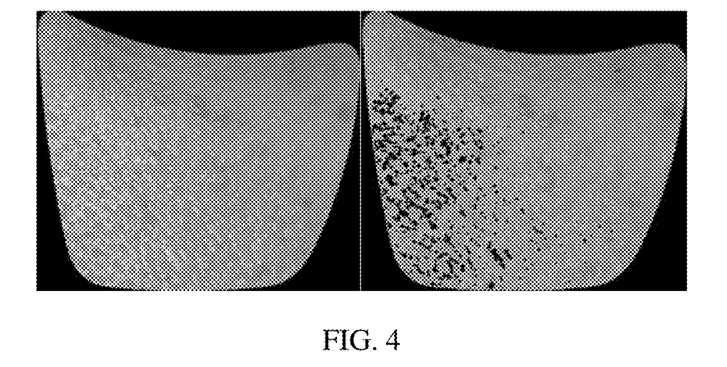
FIG. 4 is a schematic block diagram of bright light removal according to an embodiment of this application.

In other words, the bright light needs to satisfy both:

$$C_{bright\ light} >= T3 \text{ and } C_{bright\ light} - CS_{i-1} > T4,$$

where $C_{bright\ light}$ is a color of the bright light, and $C_{bright\ light}$ belongs to the $i^{th}$ type of color in the n types of colors. As shown in FIG. 4, a left picture in FIG. 4 shows the dark circle region of interest with the bright light not removed, and a right picture in FIG. 4 shows the dark circle region of interest obtained after the bright light is removed by using the foregoing formulas. It can be learned that the bright light region can be well removed by using the foregoing formulas, and that a bright light or low light region is recognized as a reference skin color region due to a comparatively light color can be avoided, thereby improving accuracy of dark circle recognition.

Optionally, T3 and T4 may be preset.

Optionally, T3 may represent a minimum value that may be set for bright light in the to-be-processed image. That is, T3 may be a darkest color of a bright light region, and the reference skin color is darker than the bright light region, that is, CS<T3 needs to be met.

In this embodiment of this application, the dark circle region in the dark circle region of interest may be determined based on the dark circle color and the reference skin color.

Optionally, whether a first pixel in the dark circle region of interest is a pixel that can be distinguished by human eyes may be determined based on a minimum contrast threshold.

For example, if the first pixel in the dark circle region of interest satisfies:

$$CS - C >= T2,$$

where the first pixel in the dark circle region of interest is a pixel that can be distinguished by human eyes. The first pixel may belong to the dark circle region, or the first pixel may belong to the reference skin color region. C is the first pixel, CS is the reference skin color, and T2 represents a minimum contrast between two colors between which human eyes can distinguish.

Optionally, T2 may be preset.

For another example, if the first pixel in the dark circle region of interest does not satisfy:

$$CS - C >= T2,$$

where the first pixel in the dark circle region of interest is a pixel that cannot be distinguished by human eyes, and the first pixel may belong to the reference skin color region. C is the first pixel, CS is the reference skin color, and T2 represents a minimum contrast between two colors between which human eyes can distinguish.

In this embodiment of this application, threshold-based determining may be performed on the first pixel in the dark circle region of interest, to determine that the first pixel belongs to the dark circle region or the reference skin color region.

For example, if the first pixel in the dark circle region of interest satisfies:

$$\frac{C - CD}{CS - C} < T1,$$

where the first pixel belongs to the dark circle region, where C is the first pixel, CD is the dark circle color, CS is the reference skin color, and T1 is a contrast of the first pixel with respect to the dark circle color and the reference skin color.

Optionally, T1 may be preset.

That is, when the first pixel satisfies $$\frac{C - CD}{CS - C} < T1,$$

a color of the first pixel is closer to a color of the dark circle region.

For another example, if the first pixel in the dark circle region of interest does not satisfy:

$$\frac{C - CD}{CS - C} < T1,$$

where the first pixel belongs to the reference skin color region, where C is the first pixel, CD is the dark circle color, CS is the reference skin color, and T1 is a contrast of the first pixel with respect to the dark circle color and the reference skin color.

Figure 5:
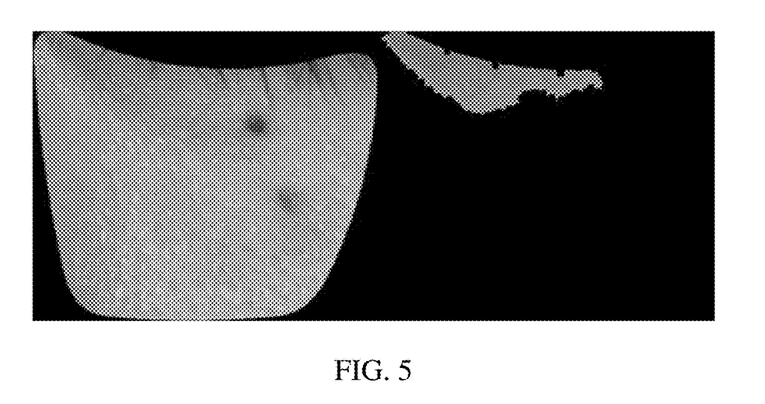
FIG. 5 is a schematic block diagram of dark circle region segmentation according to an embodiment of this application.

As shown in FIG. 5, a left picture in FIG. 5 shows the dark circle region of interest, and a right picture in FIG. 5 shows the dark circle region obtained through segmentation by using the method in this embodiment of this application. It can be learned that the dark circle region can be precisely recognized by using the method in this embodiment of this application.

Generally speaking, dark circles may be divided into structural dark circles, pigmented dark circles, vascular dark circles, and the like.

The structural dark circles are usually caused by formation of bags under eyes due to aging, and the structural dark circles usually appear in a middle position of the dark circle region of interest. Therefore, the structural dark circles can be determined according to a position.

Optionally, if a color of a middle region in the dark circle region of interest is darker than the dark circle color, the color of the middle region in the dark circle region of interest is a specific threshold darker than a color of skin surrounding the middle region, and the middle region is a non-discrete region, the middle region in the dark circle region of interest is the dark circle region. In this case, it may also be considered that the middle region in the dark circle region of interest is a starting position of dark circles. Correspondingly, it may be determined that the dark circle region of interest includes the structural dark circles.

Figure 6:
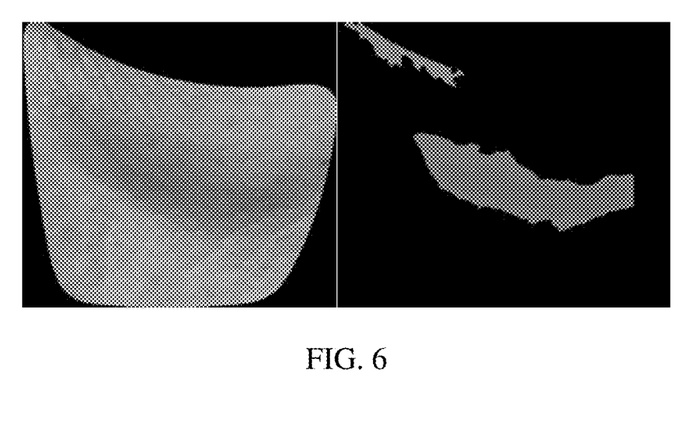
FIG. 6 is a schematic block diagram of dark circle region segmentation according to another embodiment of this application.

When the dark circle region of interest includes the structural dark circles, as shown in FIG. 6, a left picture in FIG. 6 shows the dark circle region of interest, and a right picture in FIG. 6 shows the dark circle region obtained through segmentation by using the method in this embodiment of this application. It can be learned that when the dark circles are the structural dark circles, the dark circle region may also be precisely recognized by using the method in this embodiment of this application.

S150: Obtain a dark circle evaluation result based on the dark circle region.

In this embodiment of this application, a feature of the dark circle region may be extracted, where the feature includes at least one of a contrast of the dark circle region, an area of the dark circle region, or a variance of the dark circle region; and based on the feature, a severity of dark circles may be evaluated by using a pattern recognition method.

In this embodiment of this application, the dark circle evaluation result may be obtained based on the dark circle region and the reference skin color region.

Optionally, a feature of the reference skin color region may be extracted, and based on the feature of the dark circle region and the feature of the reference skin color region, the severity of dark circles is evaluated by using the pattern recognition method. The feature of the reference skin color region includes at least one of a contrast of the reference skin color region, an area of the reference skin color region, or a variance of the reference skin color region.

Optionally, the pattern recognition method may be linear regression, support vector machine (SVM) regression, or the like. This is not limited in this embodiment of this application.

Optionally, a score indicating the severity of dark circles may be obtained by using the pattern recognition method.

Optionally, a spectrum of dark circle graphs for scoring may be created. Dark circle graphs with different grayscale values correspond to corresponding scores. For example, a score interval indicating the severity of dark circles may be 60 to 100 points, and the spectrum of dark circle graphs corresponds to the score interval.

Figure 7:
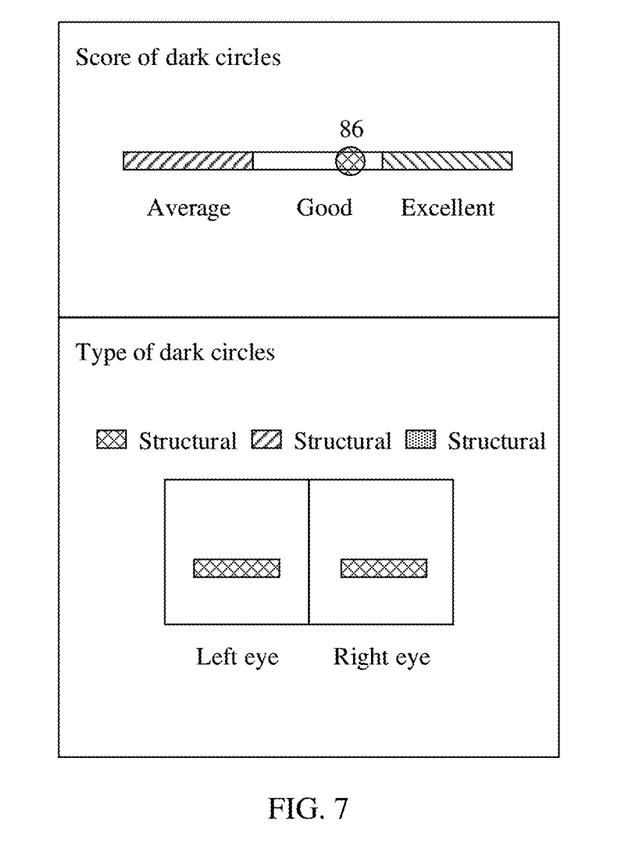
FIG. 7 is a schematic block diagram of a display interface according to an embodiment of this application.

Optionally, the terminal device may output score information of dark circles. As shown in FIG. 7, the terminal device may output the score information on a display interface of the terminal device. It should be understood that the display interface in FIG. 7 is merely an example but not a limitation.

In this embodiment of this application, a type of dark circles is determined based on a location of a region of a darkest color in the n types of colors and/or a color of the dark circle region.

Optionally, if a pixel in the dark circle region is blackish or brownish, it may be determined that the dark circles are the pigmented dark circles. If a pixel in the dark circle region is reddish or cyanic, it may be determined that the dark circles are the vascular dark circles.

In this embodiment of this application, the dark circle region may include j regions, and the j regions one-to-one correspond to j types of colors in the n types of colors, where j is an integer greater than or equal to 1 and less than n.

For example, in color space YCRCB, a Y value, a CR value, and a CB value of each type of color in the j types of colors may be extracted, where the Y value represents brightness of each type of color, the CR value represents a difference between a red component of each type of color and the brightness of each type of color, and the CB value represents a difference between a blue component of each type of color and the brightness of each type of color.

In this case, it may be determined, based on the Y value, the CR value, and the CB value of each type of color, that a type of dark circles included in the region corresponding to each type of color is the pigmented dark circles or the vascular dark circles, where the vascular dark circles include red eye circles, dark-cyan dark circles, light-cyan dark circles, light-red dark circles, or blue eye circles.

Optionally, if a color of a middle region in the dark circle region of interest is darker than the dark circle color, the color of the middle region is darker than a color of a region surrounding the middle region, and the middle region is a non-discrete region, the dark circle region includes the structural dark circles.

Optionally, if the dark circle region includes at least two types of dark circles in the vascular dark circles, the pigmented dark circles, or the structural dark circles, dark circles in the dark circle region are mixed dark circles.

Figure 8:
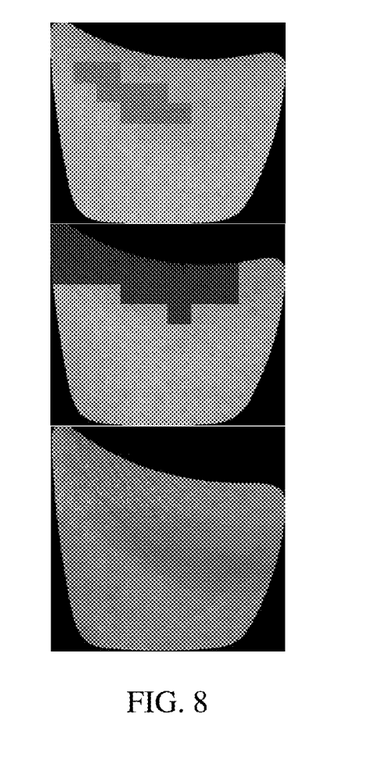
FIG. 8 is a schematic block diagram of types of dark circles according to an embodiment of this application.

In this embodiment of this application, the terminal device may output type information of dark circles. As shown in FIG. 7, the terminal device may output the type information on a display interface of the terminal device. It should be understood that the display interface in FIG. 7 is merely an example but not a limitation. The foregoing types of dark circles are shown in FIG. 8. A shadow region in an upper picture in FIG. 8 shows recognized vascular dark circles, a shadow region in a middle picture in FIG. 8 shows recognized pigmented dark circles, and a lower picture in FIG. 8 shows the structural dark circles.

Figure 9:
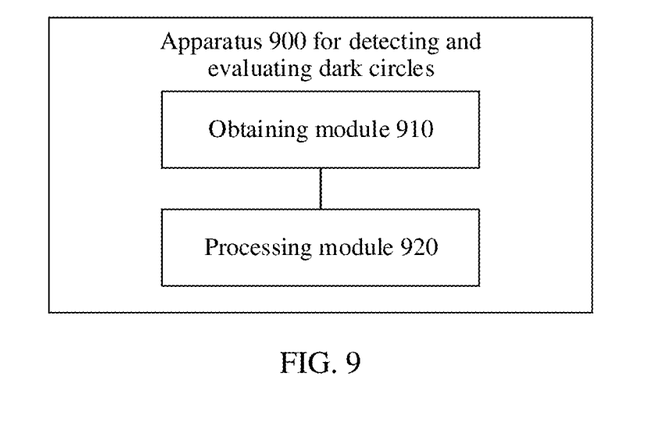
FIG. 9 is a schematic structural diagram of a dark circle detection and evaluation apparatus according to an embodiment of this application.

FIG. 9 a schematic block diagram of an apparatus 900 for detecting and evaluating dark circles according to an embodiment of this application. It should be understood that the apparatus 900 for detecting and evaluating dark circles is merely an example. The apparatus in this embodiment of this application may further include another module or unit, may include modules whose functions are similar to those of the modules in FIG. 9, or does not need to include all modules in FIG. 9.

An obtaining module 910, configured to obtain a to-be-processed image.

A processing module 920, configured to extract a dark circle region of interest from the to-be-processed image.

The processing module 920 is configured to perform color clustering on the dark circle region of interest to obtain n types of colors in the dark circle region of interest, where n is a positive integer.

The processing module 920 is configured to recognize a dark circle region in the dark circle region of interest based on the n types of colors.

The processing module 920 is configured to obtain a dark circle evaluation result based on the dark circle region.

Optionally, the processing module 920 is specifically configured to: determine a dark circle color and a reference skin color based on the n types of colors; and determine the dark circle region in the dark circle region of interest based on the dark circle color and the reference skin color.

Optionally, the processing module 920 is specifically configured to: determine a first color in the n types of colors as the dark circle color in the dark circle region of interest; and determine a second color in the n types of colors as the reference skin color in the dark circle region of interest.

Optionally, the first color is a darkest color obtained after noise is removed from the n types of colors, and the second color is a lightest color obtained after bright light is removed from the n types of colors.

Optionally, the processing module 920 is specifically configured to: If a first pixel in the dark circle region of interest satisfies:

$$\frac{C-CD}{CS-C} < T1,$$

where the first pixel belongs to the dark circle region, where C is the first pixel, CD is the dark circle color, CS is the reference skin color, and T1 is a contrast of the first pixel with respect to the dark circle color and the reference skin color.

Optionally, a first pixel in the dark circle region of interest satisfies:

$$CS-C>=T2,$$

where C is the first pixel, CS is the reference skin color, and T2 represents a minimum contrast between two colors between which human eyes can distinguish.

Optionally, the reference skin color satisfies at least one of:

$$CS<T3 \text{ or } CS-CS_{i-1}<=T4,$$

where CS is the reference skin color; CS belongs to an $i^{th}$ type of color in the n types of colors, and $CS_{i-1}$ is an $(i-1)^{th}$ type of color in the n types of colors, where i is a positive integer greater than or equal to 1 and less than or equal to n; T3 represents a minimum value of a color of a bright light region; and T4 represents a difference between the $i^{th}$ type of color and the $(i-1)^{th}$ type of color.

Optionally, the processing module 920 is specifically configured to: remove an eyelash region from the to-be-processed image; and extract the dark circle region of interest from the to-be-processed image from which the eyelash region is removed.

Optionally, the processing module 920 is specifically configured to: extract a feature of the dark circle region, where the feature includes at least one of a contrast of the dark circle region, an area of the dark circle region, or a variance of the dark circle region; and evaluate, based on the feature, a severity of dark circles by using a pattern recognition method.

Optionally, the processing module 920 is specifically configured to determine a type of dark circles based on a location of a region of a darkest color in the n types of colors and/or a color of the dark circle region.

Optionally, the dark circle region includes j regions, the j regions one-to-one correspond to j types of colors in the n types of colors, where j is an integer greater than or equal to 1 and less than n. The processing module 920 is further configured to: extract a Y value, a CR value, and a CB value of each type of color in the j types of colors, where the Y value represents brightness of each type of color, the CR value represents a difference between a red component of each type of color and the brightness of each type of color, and the CB value represents a difference between a blue component of each type of color and the brightness of each type of color; and determine, based on the Y value, the CR value, and the CB value of each type of color, that a type of dark circles included in a region corresponding to each type of color is pigmented dark circles or vascular dark circles, where the vascular dark circles include red eye circles, dark-cyan dark circles, light-cyan dark circles, light-red dark circles, or blue eye circles.

Optionally, if a color of a middle region in the dark circle region of interest is darker than the dark circle color, the color of the middle region is darker than a color of a region surrounding the middle region, and the middle region is a non-discrete region, the dark circle region includes structural dark circles.

Optionally, if the dark circle region includes at least two types of dark circles in the vascular dark circles, the pigmented dark circles, or the structural dark circles, dark circles in the dark circle region are mixed dark circles.

It should be understood that, the processor in the embodiments of this application may be a central processing unit (CPU), or may be another general-purpose processor, a digital signal processor (DSP), an application-specific integrated circuit (ASIC), a field programmable gate array (FPGA), or another programmable logical device, a discrete gate or transistor logical device, a discrete hardware component, or the like. The general-purpose processor may be a microprocessor, or the processor may be any conventional processor or the like.

It may be understood that the memory in the embodiments of this application may be a volatile memory or a nonvolatile memory, or may include a volatile memory and a nonvolatile memory. The nonvolatile memory may be a read-only memory (ROM), a programmable read-only memory (programmable ROM, PROM), an erasable programmable read-only memory (erasable PROM, EPROM), an electrically erasable programmable read-only memory (electrically EPROM, EEPROM), or a flash memory. The volatile memory may be a random access memory (RAM), used as an external cache. Through example but not limitative description, many forms of random access memory (RAM) RAMs are available, for example, a static random access memory (static RAM, SRAM), a dynamic random access memory (DRAM), a synchronous dynamic random access memory (synchronous DRAM, SDRAM), a double data rate synchronous dynamic random access memory (double data rate SDRAM, DDR SDRAM), an enhanced synchronous dynamic random access memory (enhanced SDRAM, ESDRAM), a synchronous link dynamic random access memory (synchlink DRAM, SLDRAM), and a direct rambus dynamic random access memory (direct rambus RAM, DR RAM).

All or some of the foregoing embodiments may be implemented by using software, hardware, firmware, or any combination thereof. When software is used to implement the embodiments, all or some of the foregoing embodiments may be implemented in a form of a computer program product. The computer program product includes one or more computer instructions or computer programs. When the program instructions or the computer programs are loaded and executed on a computer, the procedure or functions according to the embodiments of this application are all or partially generated. The computer may be a general-purpose computer, a dedicated computer, a computer network, or another programmable apparatus. The computer instructions may be stored in a computer-readable storage medium or may be transmitted from a computer-readable storage medium to another computer-readable storage medium. For example, the computer instructions may be transmitted from a website, computer, server, or data center to another website, computer, server, or data center in a wired (for example, infrared, radio, and microwave, or the like) manner. The computer-readable storage medium may be any usable medium accessible by a computer, or a data storage device, such as a server or a data center, integrating one or more usable media. The usable medium may be a magnetic medium (for example, a floppy disk, a hard disk, or a magnetic tape), an optical medium (for example, a DVD), or a semiconductor medium. The semiconductor medium may be a solid-state drive.

It should be understood that the term "and/or" in this specification describes only an association relationship for describing associated objects and represents that three relationships may exist. For example, A and/or B may represent the following three cases: Only A exists, both A and B exist, and only B exists. In addition, the character "/" in this specification generally indicates an "or" relationship between the associated objects.

It should be understood that sequence numbers of the foregoing processes do not mean execution sequences in the embodiments of this application. The execution sequences of the processes shall be determined according to functions and internal logic of the processes, and shall not be construed as any limitation on the implementation processes of the embodiments of this application.

A person of ordinary skill in the art may be aware that, in combination with the examples described in the embodiments disclosed in this specification, units and algorithm steps can be implemented by electronic hardware or a combination of computer software and electronic hardware. Whether the functions are performed by hardware or software depends on particular applications and design constraints of the technical solutions. A person skilled in the art may use different methods to implement the described functions for each particular application, but it shall not be considered that the implementation goes beyond the scope of this application.

It may be clearly understood by a person skilled in the art that, for the purpose of convenient and brief description, for a detailed working process of the foregoing system, apparatus, and unit, refer to a corresponding process in the foregoing method embodiments, and details are not described herein again.

In the several embodiments provided in this application, it should be understood that the disclosed system, apparatus, and method may be implemented in other manners. For example, the described apparatus embodiment is merely an example. For example, division into the units is merely logical function division and may be other division in actual implementation. For example, a plurality of units or components may be combined or integrated into another system, or some features may be ignored or not performed. In addition, the displayed or discussed mutual couplings or direct couplings or communication connections may be implemented through some interfaces. The indirect couplings or communication connections between the apparatuses or units may be implemented in electrical, mechanical, or other forms.

The units described as separate parts may or may not be physically separate, and parts displayed as units may or may not be physical units, may be located in one place, or may be distributed on a plurality of network units. Some or all of the units may be selected based on actual requirements to achieve the objectives of the solutions of the embodiments.

In addition, the functional units in the embodiments of this application may be integrated into one processing unit, or each of the units may exist alone physically, or two or more units are integrated into one unit.

When the functions are implemented in a form of a software functional unit and sold or used as an independent product, the functions may be stored in a computer-readable storage medium. Based on such an understanding, the technical solutions of this application essentially, or the part contributing to the conventional technology, or some of the technical solutions may be implemented in a form of a software product. The software product is stored in a storage medium, and includes several instructions for instructing a computer device (which may be a personal computer, a server, a network device, or the like) to perform all or some of the steps of the methods described in the embodiments of this application. The foregoing storage medium includes any medium that can store program code, such as a USB flash drive, a removable hard disk, a read-only memory (ROM), a random access memory (RAM), a magnetic disk, or an optical disc.

The foregoing descriptions are merely specific implementations of this application, but are not intended to limit the protection scope of this application. Any variation or replacement readily figured out by a person skilled in the art within the technical scope disclosed in this application shall fall within the protection scope of this application. Therefore, the protection scope of this application shall be subject to the protection scope of the claims.

What is claimed is:

1. A dark circle detection and evaluation method, comprising:
    obtaining, by a processor, a to-be-processed image;
    extracting, by the processor, a dark circle region of interest from the to-be-processed image;
    performing, by the processor, color clustering on the dark circle region of interest to obtain n types of colors in the dark circle region of interest, wherein n is a positive integer;
    determining, by the processor, a first color in the n types of colors as a dark circle color in the dark circle region of interest;
    determining, by the processor, a second color in the n types of colors as a reference skin color in the dark circle region of interest;
    determining, by the processor, a dark circle region in the dark circle region of interest based on the dark circle color and the reference skin color; and
    obtaining, by the processor, a dark circle evaluation result based on the dark circle region.

2. The method of claim 1, wherein the first color is a darkest color obtained after noise is removed from the n types of colors, and the second color is a lightest color obtained after bright light is removed from the n types of colors.

3. The method of claim 1, further comprising:
    wherein a first pixel in the dark circle region of interest satisfies:

$$\frac{C - CD}{CS - C} < T1,$$

wherein the first pixel belongs to the dark circle region, wherein C is the first pixel, CD is the dark circle color, CS is the reference skin color, and T1 is a contrast of the first pixel with respect to the dark circle color and the reference skin color.

4. The method of claim 3, wherein the first pixel satisfies:

$$CS-C >= T2,$$

wherein C is the first pixel, CS is the reference skin color, and T2 is a minimum contrast between two colors between which human eyes can distinguish.

5. The method of claim 1, wherein the reference skin color satisfies at least one of:

$$CS<T3,$$

or $$CS-CS_{i-1}<=T4,$$

wherein CS is the reference skin color, CS is an $i^{th}$ type of colors in the n types of colors, and $CS_{i-1}$ is an $(i-1)^{th}$ type of colors in the n types of colors;

wherein i is a positive integer greater than or equal to 1 and less than or equal to n;

wherein T3 is a minimum value of a color of a bright light region; and wherein T4 is a difference between the $i^{th}$ type of color and $(i-1)^{th}$ types of color.

6. The method of claim 1, further comprising:
removing an eyelash region from the to-be-processed image; and
extracting the dark circle region of interest from the to-be-processed image after the eyelash region is removed from the to-be-processed image.

7. The method of claim 1, further comprising:
extracting a feature of the dark circle region, wherein the feature comprises at least one of a contrast of the dark circle region, an area of the dark circle region, or a variance of the dark circle region; and
evaluating, based on the feature, a severity of dark circles by using a pattern recognition method.

8. The method of claim 1, wherein the dark circle region comprises j regions, the j regions one-to-one correspond to j types of colors in the n types of colors, and j is an integer greater than or equal to 1 and less than n; and the method further comprises:
for each type of color in the j types of colors, extracting a Y value, a CR value, and a CB value of the type of color, wherein the Y value represents brightness of the type of color, the CR value represents a difference between a red component of the type of color and the brightness of the type of color, and the CB value represents a difference between a blue component of the type of color and the brightness of the type of color; and
determining, based on the Y value, the CR value, and the CB value of each type of color, that a type of dark circles comprised in a region corresponding to each type of color is pigmented dark circles or vascular dark circles, wherein the vascular dark circles comprise red eye circles, dark-cyan dark circles, light-cyan dark circles, light-red dark circles, or blue eye circles.

9. The method of claim 8, wherein:
a color of a middle region in the dark circle region of interest is darker than the dark circle color,
the color of the middle region is darker than a color of a region surrounding the middle region, and
the middle region is a non-discrete region, wherein the dark circle region comprises structural dark circles.

10. The method of claim 9,
wherein the dark circle region comprises at least two types of dark circles in the vascular dark circles, the pigmented dark circles, or the structural dark circles, and
wherein dark circles in the dark circle region are mixed dark circles.

11. An electronic device, comprising:
a non-transitory memory comprising instructions; and
a processor coupled to the non-transitory memory, wherein the instructions being executed by the processor cause the electronic device to:
obtain a to-be-processed image;
extract a dark circle region of interest from the to-be-processed image;
perform color clustering on the dark circle region of interest to obtain n types of colors in the dark circle region of interest, wherein n is a positive integer;
determine a first color in the n types of colors as a dark circle color in the dark circle region of interest;
determine a second color in the n types of colors as a reference skin color in the dark circle region of interest;
determine a dark circle region in the dark circle region of interest based on the dark circle color and the reference skin color; and
obtain a dark circle evaluation result based on the dark circle region.

12. The electronic device of claim 11, wherein the first color is a darkest color obtained after noise is removed from the n types of colors, and the second color is a lightest color obtained after bright light is removed from the n types of colors.

13. The electronic device of claim 11, wherein a first pixel in the dark circle region of interest satisfies:

$$\frac{C-CD}{CS-C} < T1,$$

wherein the first pixel belongs to the dark circle region, wherein C is the first pixel, CD is the dark circle color, CS is the reference skin color, and T1 is a contrast of the first pixel with respect to the dark circle color and the reference skin color.

14. The electronic device of claim 13, wherein the first pixel satisfies:

$$CS-C >= T2,$$

wherein C is the first pixel, CS is the reference skin color, and T2 is a minimum contrast between two colors between which human eyes can distinguish.

15. The electronic device of claim 11, wherein the reference skin color satisfies at least one of:

$$CS<T3,$$

or $$CS-CS_{i-1} <= T4,$$

wherein CS is the reference skin color, CS is an $i^{th}$ type of colors in the n types of colors, and $CS_{i-1}$ is an $(i-1)^{th}$ type of colors in the n types of colors;
wherein i is a positive integer greater than or equal to 1 and less than or equal to n;
wherein T3 is a minimum value of a color of a bright light region; and
wherein T4 is a difference between the $i^{th}$ type of color and $(i-1)^{th}$ types of color.

16. The electronic device of claim 11, wherein the instructions further cause the electronic device to:
remove an eyelash region from the to-be-processed image; and
extract the dark circle region of interest from the to-be-processed image after the eyelash region is removed from the to-be-processed image.

17. The electronic device of claim 11, wherein the instructions being executed by the processor further cause the electronic device to:
extract a feature of the dark circle region, wherein the feature comprises at least one of a contrast of the dark circle region, an area of the dark circle region, or a variance of the dark circle region; and
evaluate, based on the feature, a severity of dark circles by using a pattern recognition method.

18. The electronic device of claim 11, wherein the dark circle region comprises j regions, the j regions one-to-one correspond to j types of colors in the n types of colors, and j is an integer greater than or equal to 1 and less than n; and the method further comprises:

for each type of color in the j types of colors, extracting a Y value, a CR value, and a CB value of the type of color, wherein the Y value represents brightness of the type of color, the CR value represents a difference between a red component of the type of color and the brightness of the type of color, and the CB value represents a difference between a blue component of the type of color and the brightness of the type of color; and     determining, based on the Y value, the CR value, and the CB value of each type of color, that a type of dark circles comprised in a region corresponding to each type of color is pigmented dark circles or vascular dark circles, wherein the vascular dark circles comprise red eye circles, dark-cyan dark circles, light-cyan dark circles, light-red dark circles, or blue eye circles.

19. The electronic device of claim 18, wherein:

a color of a middle region in the dark circle region of interest is darker than the dark circle color, the color of the middle region is darker than a color of a region surrounding the middle region, and the middle region is a non-discrete region, wherein the dark circle region comprises structural dark circles.

20. The electronic device of claim 19, wherein the dark circle region comprises at least two types of dark circles in the vascular dark circles, the pigmented dark circles, or the structural dark circles, and wherein dark circles in the dark circle region are mixed dark circles.

\* \* \* \* \*

UNITED STATES PATENT AND TRADEMARK OFFICE
CERTIFICATE OF CORRECTION

PATENT NO. : 11,779,264 B2  
APPLICATION NO. : 17/297684  
DATED : October 10, 2023  
INVENTOR(S) : Yao et al.

Page 1 of 1

It is certified that error appears in the above-identified patent and that said Letters Patent is hereby corrected as shown below:

On the Title Page

Applicant (71): "Honor Device Co., Ltd., Guangdong (CN)" should read -- Honor Device Co., Ltd., Shenzhen (CN) --.

Signed and Sealed this  
Fourteenth Day of November, 2023

Katherine Kelly Vidal  
*Director of the United States Patent and Trademark Office*